United States Patent [19]

Bonjouklian et al.

[11] Patent Number: 4,870,185
[45] Date of Patent: Sep. 26, 1989

[54] HAPALINDOLES

[75] Inventors: Rosanne Bonjouklian, Zionsville, Ind.; Richard E. Moore, Honolulu, Hi.; Jon S. Mynderse, Indianapolis, Ind.; Gregory M. L. Patterson, Honolulu, Hi.; Tim A. Smitka, Indianapolis, Ind.

[73] Assignees: Eli Lilly and Company, Indianapolis, Ind.; University of Hawaii, Honolulu, Hi. ; a part interest

[21] Appl. No.: 908,746

[22] Filed: Sep. 18, 1986

[51] Int. Cl.$^4$ ................... C07D 513/06; C07D 209/80
[52] U.S. Cl. .................................... 548/148; 435/119; 548/425; 548/469
[58] Field of Search ........................ 548/469, 148, 425

[56] References Cited

U.S. PATENT DOCUMENTS 4,755,610  7/1988  Moore et al. ....................... 548/425

FOREIGN PATENT DOCUMENTS 171283  2/1986  European Pat. Off. ............ 548/420

OTHER PUBLICATIONS

Biol. Abstr. 51:45694 Abstracting O. P. Sachkova et al., "Problem on the Interspecies Antagonism of Cyanophyta Representatives," Vest. Akad. nauk Kazakh, S.S.R. 25 (5) 69–71 (1969).
P. N. Srivastava, "Taxonomy and Biology of Blue--Green Algae," T. V. Desikachary, ed., U. Madras, 1972, pp. 391–392.
J. Isaklidis et al., Chem. Abst., vol. 87, No. 84758k (1977).
R. Moore et al., J. Am. Chem. Soc. (1984), 106, 6456–6457.

Primary Examiner—Mary E. Ceperley
Attorney, Agent, or Firm—Nancy J. Harrison; Leroy Whitaker

[57] ABSTRACT

New alkaloids called hapalindoles J-Q and T-V, which are antibacterial and antifungal agents, and methods of preparing these alkaloids by culturing the blue-green alga *Hapalosiphon fontinalis* ATCC 39694, are provided.

13 Claims, No Drawings

HAPALINDOLES

This invention was made with the support of the Government under Grant No. CHE83-03996 awarded by the National Science Foundation. The Government has certain rights in this invention.

SUMMARY OF THE INVENTION

This invention relates to new alkaloids from the blue-green alga (cyanobacterium) *Hapalosiphon fontinalis* ATCC 39694. The new alkaloids, called hapalindoles J-Q and T-V, are antibacterial and antifungal agents. In another aspect, this invention relates to methods of preparing these alkaloids by culturing *H. fontinalis* ATCC 39694 and isolating the new hapalindoles by chromatographic procedures.

DETAILED DESCRIPTION

This invention relates to new antibacterial and antifungal agents. In particular, this invention provides useful new alkaloids, called hapalindoles J, K, L, M, N, O, P, Q, T, U and V. Hapalindoles A-I were described by Richard E. Moore and Gregory M. L. Patterson in application Ser. No. 638,847, filed Aug. b 8, 1984, which was abandoned in favor of continuation-in-part application Ser. No. 648,114, filed Sept. 7, 1984, which was also abandoned in favor of copending continuation application Ser. No. 829,632, filed Feb. 14, 1986, now U.S. Pat. No. 4,755,610 which is incorporated herein by reference. Like hapalindoles A-I, the new hapalindoles J-Q and T-V can be prepared by culturing the blue-green green alga *Hapalosiphon fontinalis* ATCC 39694. The new alkaloids of this invention have been assigned the structures shown infra. The numbering system used to descibe the new compounds differs from the system used to describe hapalindoles A-I in application Ser. No. 829,632. The new hapalindoles have the following structures and numbering system:

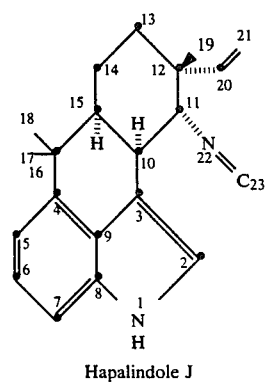

Hapalindole J

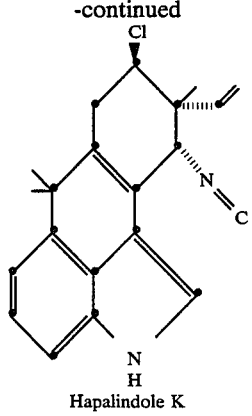

Hapalindole K

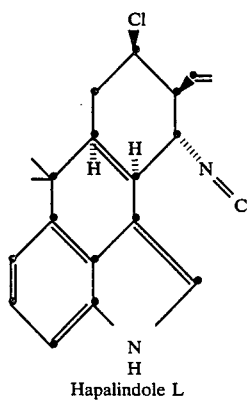

Hapalindole L

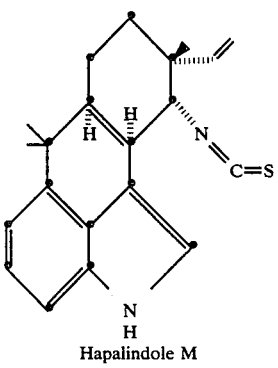

Hapalindole M

In hapalindoles N and P, the hydrogen on the carbon bearing the epoxide is in the "R" chirality in one and in the "S" chirality in the other; however, the exact chirality of N and P has not yet been determined:

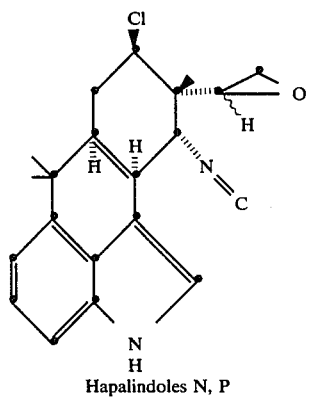

Hapalindoles N, P

-continued

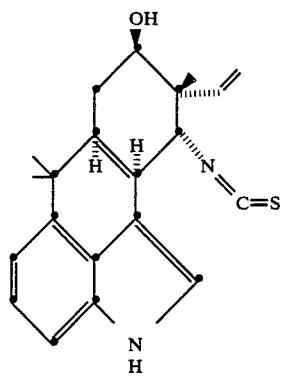

Hapalindole O

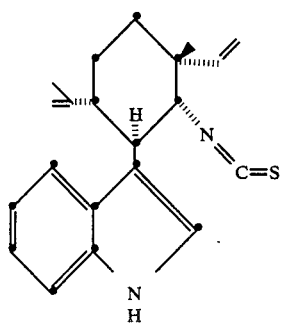

Hapalindole Q

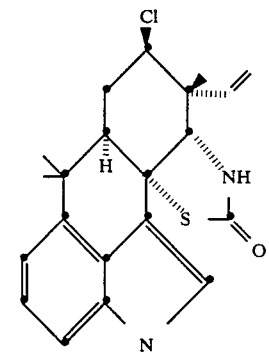

Hapalindole T

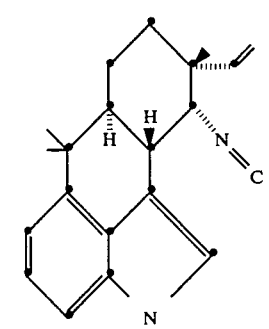

Hapalindole U

-continued

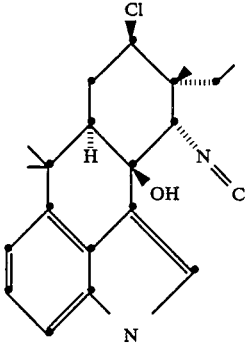

Hapalindole V

The hapalindoles of this invention are produced, along with the hapalindoles previously described by Moore and Patterson, by cultivating a hapalindole-producing strain of the blue-green alga *Hapalosiphon fontinalis* (Ag.) Bornet (Stigonemataceae). This strain has been deposited and made part of the stock culture collection of The American Type Culture Collection, 12301 Parklawn Drive, Rockville, Md. 20852, from which it is available to the public under the accession number ATCC 39694.

As is the case with other organisms, the characteristics of *Hapalosiphon fontinalis* ATCC 39694 are subject to variation. Thus, progeny of the ATCC 39694 strain, e.g. recombinants, variants and mutants, may be obtained by recognized procedures. Exemplary procedures include treatment with various known physical and chemical mutagens, such as ultraviolet rays, X-rays, gamma rays, and N-methyl-N'nitro-N-nitrosoguanidine. Progeny of *Hapalosiphon fontinalis* ATCC 39694 which retain the characteristic of producing a hapalindole selected from J–Q and T–V may be used in this invention.

The hapalindole alkaloids of this invention are prepared by culturing the *Hapalosiphon fontinalis* strain under submerged aerobic conditions in a suitable culture medium until substantial antibiotic activity is produced. Other culture techniques, such as surface growth on solidified media, can also be used to produce these compounds. The culture medium used to grow *Hapalosiphon fontinalis* ATCC 39694 can be any one of a number of media. Economy in production, optimal yield, and ease of product isolation are factors to consider when choosing the carbon sources and nitrogen sources to be used. Among the nutrient inorganic salts which can be incorporated in the culture media are the customary soluble salts capable of yielding iron, potassium, sodium, magnesium, calcium, ammonium, chloride, carbonate, phosphate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of the hapalindoles, submerged aerobic cultivation in tanks can be used. Small quantities may be obtained by shake-flask culture. Because of the time lag in antibiotic production commonly associated with inoculation of large tanks with the organism, it is preferable to use a vegetative inoculum. The vegetative inoculum is prepared by inoculating a small volume of culture medium with the spore or akinete-containing form or fragments of the vegetative trichome of the organism to obtain a fresh, actively growing culture of the organism. The vegetative inoculum is then transferred to a larger tank. The medium used for the vegetative inoculum can be the same as that used for larger fermentations, but other media can also be used.

*H. fontinalis* ATCC 39694 can be grown at temperatures between about 20° and about 30° C. The hapalindole compounds are produced at a temperature of about 24° C. and an incident illumination intensity of 330 microEinsteins-m$^2$-sec$^{-1}$. Light intensities somewhat higher or lower can also be used to produce these compounds.

As is customary in aerobic submerged culture processes of this type, $CO_2$ in sterile air is bubbled through the culture medium. For efficient production of the hapalindoles, the percent of $CO_2$ should be about 1% (at 24° C. and one atmosphere of pressure).

Hapalindole production can be followed during the cultivation by testing samples of the broth against organisms known to be sensitive to these antibiotics. One useful assay organism is *Staphylococcus aureus*.

Following their production under submerged aerobic cultivation conditions, the hapalindoles can be recovered from the cultivation medium by methods used in this art. Recovery is generally accomplished by initially filtering the culture medium to separate the algal cells and then freeze drying the separated cells. The freeze-dried alga can be extracted with a suitable solvent such as isopropanol, dichloromethane, or ethyl acetate. The alkaloids can be separated by subjecting this extract to gel filtration and/or silica-gel chromatography. The alkaloids can be purified by high-performance liquid chromatography (HPLC).

The hapalindoles of this invention inhibit the growth of various pathogenic bacteria and fungi. Table 1 summarizes the diameter (mm) of zones of inhibition of growth of certain organisms, as determined by standard agar-disk diffusion assays.

Preparation 1

Culture of Hapalosiphon fontinalis ATCC 39694

*Hapalosiphon fontinalis* strain V-3-1 (ATCC was cultured in 25-L glass bottles containing an inorganic medium having the following composition:

| Ingredient | Amount |
|---|---|
| $NaNO_3$ | 200 mg/L |
| $NH_4Cl$ | 10 mg/L |
| $K_2HPO_4.3H_2O$ | 65 mg/L |
| $MgSO_4.7H_2O$ | 50 mg/L |
| $CaCl_2.2H_2O$ | 13 mg/L |
| 3-(N—morpholino)-propanesulfonic acid | 627 mg/L |
| Minor elements solution[a] | 1 mL/L |
| Trace elements solution[b] | 3/25 (0.12) mL/L |

Prior to autoclaving, the pH of the complete medium is adjusted to 7 with sodium hydroxide.

| [a]Minor Elements Solution: | |
|---|---|
| Ingredient | Amount |
| $FeCl_3.6H_2O$ | 0.54 g/L |
| $Na_2EDTA$ | 3.0 g/L |
| $H_3BO_3$ | 0.62 g/L |
| $MnCl_2.4H_2O$ | 1.4 g/L |
| $ZnCl_2$ | 0.10 g/L |
| $CoCl_2.6H_2O$ | 5 mg/L |
| $CuCl_2.2H_2O$ | 34 mcg/L |

| [b]Trace Elements Solution: | |
|---|---|
| Ingredient | Amount (mg/10 L of 0.1 N $H_2SO_4$) |
| $MoO_3$ (85%) | 176.4 |
| $NH_4VO_3$ | 229.6 |
| $Cr_2K_2(SO_4)_4.24H_2O$ | 960.2 |
| $NiSO_4.6H_2O$ | 447.8 |
| $Co(NO_3)_2.6H_2O$ | 493.8 |
| $Na_2WO_4.2H_2O$ | 179.4 |
| $Al_2(SO_4)_3$ | 317.1 |
| $As_2O_3$ | 66.1 |
| $CdCl_2$ | 81.5 |
| $SrSO_4$ | 104.9 |
| $HgCl_2$ | 67.7 |
| $PbCl_2$ | 67.1 |
| LiCl | 305.5 |
| $Rb_2SO_4$ | 78.1 |
| NaBr | 64.4 |
| KI | 65.4 |

TABLE 1

In Vitro Antibacterial and Antifungal Activity of Hapalindoles

| Organism | \multicolumn{10}{c}{Diameter of Zones of Inhibition of Growth (mm)* Hapalindole} |
|---|---|---|---|---|---|---|---|---|---|---|
| | J | K | L | M | N,P | O | Q | T | U | V |
| *Staphylococcus aureus* X1.1 | 19 | 15 | 18 | T | 36 | 17 | 10 | 14 | 10 | 17 |
| *Bacillus subtilis* X12 | 21 | 14 | 20 | T | 30 | 15 | 13 | 15 | — | 25 |
| *Micrococcus luteus* X186 | 20 | 21 | 16 | T | 42 | 30 | 16 | 23 | 21 | 32 |
| *Streptococcus pneumoniae* X647 | — | — | — | 17 | 10 | 10 | 15 | T | — | T |
| *Proteus vulgaris* X45 | 21 | 17 | 12 | — | 17 | — | — | — | — | 14 |
| *Salmonella gallinarum* X142 | 17 | 16 | 16 | — | 28 | — | — | — | 11 | 32 |
| *Escherichia coli* X161 | 17 | 15 | 10 | — | 22 | T | — | T | — | T |
| *Escherichia coli* X580 | 19 | 11 | 14 | — | 31 | 18 | — | T | T | 29 |
| *Saccharomyces pastorianus* X52 | 17 | 15 | 15 | — | 22 | 11 | T | 12 | 20 | 22 |
| *Neurospora crassa* X846 | 23 | 15 | 15 | — | 22 | T | — | T | 12 | 22 |
| *Candida albicans* X657 | 16 | 19 | 15 | — | 20 | — | — | T | T | 17 |

*Disk impregnated with solution of the compound at a concentration of 1 mg/mL in MeOH. "T" = trace; "—" = inactive.

In order to illustrate this invention, the following examples are provided.

-continued

| bTrace Elements Solution: | |
|---|---|
| Ingredient | Amount (mg/10 L of 0.1 N $H_2SO_4$) |
| NaF | 110.5 |
| $Na_2SeO_4$ | 119.4 |
| $Be(NO_3)_2.3H_2O$ | 1037.0 |

Cultures were illuminated continuously at an incident intensity of 330 microEinsteins-m$^{-2}$-sec$^{-1}$ from banks of cool-white fluorescent tubes. Cultures were vigorously aerated with 1% $CO_2$ in air and incubated at 24°±1° C. Alga was cultured for 24 days and then was harvested by filtration; yields typically were 0.4–0.5 g dry weight of cells per liter of culture.

EXAMPLE 1

A. Isolation of Hapalindoles A–Q and T–V

Freeze-dried alga prepared as in Example 1 (149 g) was extracted with 1:1 CH (2×4.5 L) overnight under refrigeration with stirring. The filtered extracts were combined and concentrated under reduced pressure to give a dry green solid (21.9 g).

A portion of this solid (11 g) was dissolved in 1 L of $CH_2Cl_2$ and applied to a column (10 cm dia.×4.5 cm; 350 mL) of silica gel (EM Science Kieselgel 60; 230–400 mesh) equilibrated in $CH_2Cl_2$. The first 400 mL of effluent was discarded. Then, a 600-mL fraction of column eluate was collected and concentrated under reduced pressure to give a dry solid (1.15 g). The column was then eluted with 1:1 $CH_2Cl_2$/heptane (1 L). The collected eluate (1 L) was concentrated under reduced pressure to give a dry solid (4.8 g). Further elution of the column with $CHCl_3$ (600 mL) yielded an additional fraction which was concentrated to give 600 mg of dry solid. Further elution with 1:1 $CH_2Cl_2$/EtOAc (1 L) yielded a fraction which was concentrated to give 1.27 g of solid. A repeat flush with the same solvent system afforded an additional 0.445 g of solid having a similar composition.

The remaining portion of dry green solid (10.9 g) was subjected to a similar silica-gel chromatography to give two dried preparations (2.36 g, 3.07 g). Elution with $CHCl_3$ (500 mL) yielded an additional fraction which was concentrated to dry solid (0.85 g). Further elution with 1:1 $CH_2Cl_2$/EtOAc (1 L) yielded a fraction which was concentrated to give 2.3 g of dry solid. Again, further elution with an equal volume of solvent afforded an additional 0.545 g of material.

The first two dried preparations from each silica column were individually treated with 1:1 cyclohexane/$CH_2Cl_2$ to obtain crystalline hapalindole A (3.36 g: combined yield) directly. The mother liquors were then combined; a portion (2.3 g) was dissolved in EtOAc (25 mL) and applied to a PrepPak-500 silica cartridge in a Waters Prep LC 500A System. Material was eluted using 8 L of a hexane→85:15 hexane/EtOAc gradient. Fractions (400 mL) were collected and pools were generated on the basis of TLC analysis.

The hapalindoles had the approximate TLC Rf values shown in Table 2, using Merck Silica Gel 60 (F254) plates where the solvent systems were 2:1 hexane/EtOAc (A), 4:1 CH (B), 4:1 hexane/EtOAc (C), 2:1 CH (D) and 2:1 heptane/THF (E).

TABLE 2

| TLC Rf Values of Hapalindoles | | |
|---|---|---|
| Hapalindole | Rf Value | Solvent System |
| A | 0.45 | A |
| B | 0.51 | A |
| C | 0.64 | A |
| D | 0.76 | A |
| E | 0.61 | A |
| F | 0.58 | A |
| G | 0.46 | A |
| H | 0.67 | A |
| I | 0.58 | A |
| J | 0.44 | B |
| K | 0.36 | B |
| L | 0.26 | C |
| M | 0.53 | D |
| N | 0.12 | E |
| O | 0.2 | E |
| P | 0.15 | E |
| Q | 0.55 | C |
| T | 0.11 | E |
| U | 0.47 | A |
| V | 0.29 | E |

Pools were then individually chromatographed over a 1″×50-cm stainless-steel HPLC column containing LPS-1 silica gel (13–24 μm) at a flow rate of 2.5 mL/min, monitoring by UV at 235 nm and using the solvent systems indicated.

Pool 1 (37 mg, 1:1 $CH_2Cl_2$/heptane) afforded hapalindole Q (20 mg), hapalindole D (5 mg) and hapalindole F (8 mg).

Pool 2 (1.07 g, 1:1 $CH_2Cl_2$/heptane) yielded hapalindole M (60 mg), hapalindole B (22 mg), hapalindole U (10 mg), hapalindole Q (3 mg), a 1:1 mixture of hapalindoles C and E (460 mg), hapalindole H (150 mg) and hapalindole I (10 mg).

Pool 3 (273 mg, 2:1 $CH_2Cl_2$/heptane) gave hapalindole B (200 mg).

Pool 4 (452 mg, 4:1 $CH_2Cl_2$/heptane) gave hapalindole B (55 mg), hapalindole J (70 mg) and hapalindole K (35 mg).

Pool 5 (124 mg, 3:1 $CH_2Cl_2$/heptane) yielded hapalindole G (14 mg), hapalindole L (11 mg), hapalindole J (13 mg) and hapalindole K (7 mg).

Pool 6 (162 mg, 2:1 $CH_2Cl_2$/heptane) gave hapalindole A (160 mg).

Similarly, a portion (1.8 g) of the $CH_2Cl_2$/-EtOAc dry preparation was fractionated over a gravity column (5×12 cm) containing Merck silica (200–400 mesh) equilibrated with 2:1 $CH_2Cl_2$/cyclohexane. A gradient from 2:1 $CH_2Cl_2$/cyclohexane→100:1 $CH_2Cl_2$/$CH_3OH$ was used. Pools were generated using analytical TLC profiles (50:1 $CH_2Cl_2$/$CH_3OH$) of the eluted fractions. Fractions with Rf values of 0.4–0.5 were further purified over a 1″×50-cm stainless-steel column containing Whatman LPS-1 silica (13–24 μm) and using 7:1 heptane/THF as the eluting solvent. Thus, 290 mg of concentrate afforded hapalindole N (7 mg), hapalindole O (35 mg), hapalindole V (27 mg), hapalindole P (4 mg) and hapalindole T (45 mg).

The order of elution of all hapalindoles (Table 3) was determined using the following analytical HPLC system:

Column Support: DuPont Zorbax silica (4.6 mm×25 cm)

System: 5:1 isooctane/THF (Solvent A) or 5:2 isooctane/THF (solvent B)

Flow Rate: 1 mL/min

Detection: UV at 235 nm

TABLE 3

HPLC Retention Times for Hapalindoles

| Hapalindole | Retention Time (min) | Solvent System |
|---|---|---|
| A | 19.5 | A |
| B | 16.3 | A |
| C | 9.1 | A |
| D | 6.5 | A |
| E | 10.1 | A |
| F | 7.0 | A |
| G | 19.0 | A |
| H | 7.3 | A |
| I | 9.0 | A |
| J | 14.1 | A |
| K | 13.0 | A |
| L | 15.7 | A |
| M | 12.9 | A |
| N | 13.9 | B |
| O | 9.9 | B |
| P | 14.6 | B |
| Q | 10.9 | A |
| T | 13.2 | B |
| U | 15.8 | A |
| V | 11.4 | B |

Characteristics of Hapalindoles J-Q and T-V $^1$H NMR data for hapalindoles J-Q and T-V are presented in Tables 3-8. Other physical characteristics of the new hapalindoles are as follows:

1. Hapalindole J
Empirical formula: $C_2H_{24}N_2$;
$[\alpha]_D^+$: 54.4° (CHCl$_3$, c 0.9);
UV $\lambda_{max}$ (MeOH) 222 nm ($\epsilon$ 38,700), 280 (6,980), 291 (5,700)
IR (CHCl$_3$): 3480, 2143 cm$^{-1}$
High resolution EIMS: m/z 304.1949
FDMS: m/z 304.

2. Hapalindole K
Empirical formula: $C_2H_{31}N_2Cl$;
$[\alpha]_D$: −12.5° (CHCl$_3$, c 1.8);
UV $\lambda_{max}$ (MeOH): 226 nm ($\epsilon$ 19,900), 301 (9,960);
IR (CHCl$_3$): 3476, 2139 cm$^{-1}$
High resolution EIMS: m/z 336.1402
FDMS: m/z(rel. intensity) 336(100), 338(31).

3. Hapalindole L
Empirical formula: $C_{21}H_{23}N_2Cl$;
$[\alpha]_D$: −74.0° (CHCl$_3$, c 1.1);
IR (CHCl$_3$): 3477, 2140 c$^{-1}$
High resolution EIMS: m/z 338.1559
FDMS: m/z(rel. intensity) 338(100), 340(28).

4. Hapalindole M
Empirical formula: $C_{21}H_{24}N_2S$;
$[\alpha]_D$: −83.1° (CHCl$_3$, c 1.8);
UV $\lambda_{max}$ (MeOH) 223 nm ($\epsilon$ 41,400), 281 (7,300), 291 (5,900):
IR (CHCl$_3$): 3478, 2156, 2077 cm$^{-1}$
High resolution EIMS: m/z 336.1657
FDMS: m/z 336.

5 Hapalindole N*
*Exact structural assingment of epoxide stereo-chemistry has not yet been accomplished.
Empirical formula: $C_{21}H_{23}ClN_2O$;
$[\alpha]_D$: −31.5° (CHCl$_3$, c 1.7);
IR (CHCl$_3$): 3476, 2138 cm$^{-1}$
High resolution EIMS: m/z 354.1523
FDMS: m/z 354.

Hapalindole O
Empirical formula: $C_{24}H_{24}N_2OS$;
$[\alpha]_D$: −106.0 (CHCl$_3$, c 2.4);

UV $\lambda_{max}$ (MeOH) 222 nm ($\epsilon$ 38,900), 281 (6,969), 291 (5,733)
IR (CHCl$_3$): 3700, 3478, 2152, 2073 cm$^{-1}$
High resolution EIMS: m/z 352.1609
FDMS: m/z 352.

7. Hapalindole P*
*Exact structural assignment of epoxide stereo-chemistry has not yet been accomplished.
Empirical formula: $C_{21}H_{23}ClN_2O$;
$[\alpha]_D$: −16.3° (CHCl$_3$, c 0.8);
UV $\lambda_{max}$ (MeOH): 220 nm ($\epsilon$ 17,206), 280 (2,518)
IR (CHCl$_3$): 3475, 2138 cm$^{31\ 1}$
FDMS: m/z 354.

8. Hapalindole Q
Empirical formula: $C_{21}H_{24}N_2S$;
$[\alpha]_D$: +24.1° (CH$_2$Cl$_2$, c 1.1);
IR (CHCl$_3$): 3479, 2184, 2096 cm$^{-1}$
High resolution EIMS: m/z 336.1659
FDMS: m/z 336.

9. Hapalindole T
Empirical formula: $C_{21}H_{24}ClN_2OS$;
$[\alpha]_D$: −137° (CH$_2$Cl$_2$, c 1.5)
UV $\lambda_{max}$ (MeOH): 222 nm ($\epsilon$ 35,400), 283 (7,141)
IR (CHCl$_3$): 3477, 3400, 1679 cm$^{-1}$
High resolution FABMS: m/z 387.1299 (M+1)
FDMS: m/z 386.

10. Hapalindole U
Empirical formula: $C_{21}H_{24}N_2$;
$[\alpha]_D$: +12° (CH$_2$Cl$_2$, c 0.6)
IR (CHCl$_3$): 3479, 2145 cm$^{-1}$
High resolution FABMS: m/z 305.1996 (M+1)
FDMS: m/z 305 (M+1)

11. Haoalindole V
Empirical formula: $C_{21}H_{23}ClN_2O$;
UV $\lambda_{max}$ (MeOH) 220 nm ($\epsilon$ 34,012), 279 (5,752), 290 (4,501);
IR (CHCl$_3$): 3600, 3480, 2140 cm$^{-1}$;
High resolution FABMS: m/z 355.1599 (M+1)
FDMS: m/z 354.

TABLE 3

$^1$H NMR Data for Hapalindoles J, L, M, O in CDCl$_3$

| | $\delta$, Chemical Shift, ppm | | | |
|---|---|---|---|---|
| Position | J | M | O | L |
| 1 | 8.00 br | 7.99 | 8.055 | 8.042 |
| 2 | 6.884 br t | 6.876 | 6.855 | 6.685 |
| 5 | 6.924 m | 6.962 | 6.956 | 6.963 |
| 6 | 7.174 m | 7.173 | 7.173 | 7.182 |
| 7 | 7.177 m | 7.177 | 7.176 | 7.195 |
| 10eq | 3.845 br m | 3.834 | 3.844 | 3.853 |
| 11eq | 4.168 br d | 4.277 | 4.452 | 4.399 |
| 13ax | 1.883 td | 1.832 | 3.987 | 4.185 ddd |
| 13eq | 1.367 br dt | 1.404 | | |
| 14ax | 1.107 br q | 1.125 | 1.122 | 1.516 |
| 14eq | 1.724 br dq | 1.740 | 1.910 | 2.085 |
| 15ax | 2.099 dt | 2.007 | 2.213 | 2.304 |
| 17 | 1.514 s | 1.519 | 1.552 | 1.549 |
| 18 | 1.211 s | 1.215 | 1.208 | 1.207 |
| 19 | 0.800 s | 0.789 | 0.737 | 1.502 |
| 20 | 6.038 dd | 5.989 | 6.081 | 5.463 |
| 21E | 5.130 br d | 5.124 | 5.362 | 5.125 |
| 21Z | 5.065 br d | 5.054 | 5.257 | 4.939 |

TABLE 4

$^1$H NMR Data for Hapalindole K in CDCl$_3$

| Position | $\delta$, Chemical Shift, ppm |
|---|---|
| 1 | 7.924 br |
| 2 | 7.155 d |
| 5 | 7.004 dd |
| 6 | 7.240 dd |
| 7 | 7.131 dd |

TABLE 4-continued

¹H NMR Data for Hapalindole K in CDCl₃

| Position | δ, Chemical Shift, ppm |
|---|---|
| 11ax | 4.493 br |
| 13eq | 4.427 dd |
| 14ax | 2.700 br dd |
| 14eq | 3.079 ddd |
| 17 | 1.482 s |
| 18 | 1.495 s |
| 19 | 1.319 s |
| 20 | 6.154 dd |
| 21Z | 5.422 dd |
| 21E | 5.382 dd |

TABLE 5

¹H NMR Data for Hapalindoles N and P in Acetone-d₆

| | δ, Chemical Shift, ppm | |
|---|---|---|
| Position | N | P |
| 1 | 8.028 br | 8.029 |
| 2 | 7.289 br t | 7.317 |
| 5 | 6.934 br dd | 6.932 |
| 6 | 7.104 dd | 7.105 |
| 7 | 7.211 br dd | 7.213 |
| 10eq | 3.850 br m | 3.920 |
| 11eq | 4.916 br d | 4.805 |
| 13ax | 4.560 dd | 4.512 |
| 14ax | 1.387 q | 1.370 |
| 14eq | 2.148 dtd | 2.152 |
| 15ax | 2.372 ddd | 2.393 |
| 17 | 1.593 s | 1.590 |
| 18 | 1.199 s | 1.201 |
| 19 | 0.566 s | 0.562 |
| 20 | 3.095 dd | 3.185 br t |
| 21Z | 2.775 dd | 2.785 m |
| 21E | 2.703 dd | 2.781 m |

TABLE 6

¹H NMR Data for Hapalindole Q in CDCl₃

| Position | δ, Chemical Shift, ppm |
|---|---|
| 1 | 7.991 br |
| 2 | 6.989 d |
| 4 | 7.631 br d |
| 5 | 7.159 td |
| 6 | 7.083 td |
| 7 | 7.337 br d |
| 10ax | 3.120 br t |
| 11ax | 3.858 br d |
| 13ax | 1.51-1.62 m |
| 13eq | 1.985 dt |
| 14ax | 1.818 qd |
| 14eq | 1.5-1.62 m |
| 15ax | 2.760 br m |
| 18Z | 4.498 br |
| 18E | 4.494 br |
| 17 | 1.487 br s |
| 19 | 1.217 s |
| 20 | 6.211 dd |
| 21E | 5.361 br d |
| 21Z | 5.266 dd |

TABLE 7

¹H NMR Data for Hapalindole T in CDCl₃

| Position | δ, Chemical Shift, ppm |
|---|---|
| 1 | 8.33 br |
| 2 | 7.253 d |
| 5 | 6.990 m |
| 6 | 7.200 m |
| 7 | 7.213 m |
| 11eq | 4.553 br d |
| 13ax | 4.497 dd |
| 14ax | 1.529 q |
| 14eq | 2.313 dt |
| 15ax | 2.738 dd |
| 17 | 1.591 s |
| 18 | 1.432 s |
| 19 | 0.691 s |
| 20 | 5.866 dd |
| 21Z | 5.322 br d |
| 21E | 5.369 br d |
| 22 | 5.63 br |

TABLE 8

¹H NMR Data for Hapalindole U in CDCl₃

| | δ, Chemical Shift, ppm | |
|---|---|---|
| Position | U | V |
| 1 | 8.022 br | 8.144 br |
| 2 | 6.898 t | 7.067 d |
| 5 | 7.021 m | 7.104 dd |
| 6 | 7.165 m | 7.235 t |
| 7 | 7.178 m | 7.178 dd |
| 10ax | 3.268 br dm | |
| 11eq | 4.088 br d | 4.106 br s |
| 13ax | 1.56-1.71 m | 4.395 dd |
| 13eq | 1.56-1.71 m | |
| 14ax | 1.60 m | 2.510 m |
| 14eq | 1.92-2.05 m | 2.24-2.34 m |
| 15ax | 1.91 td | 2.24-2.34 m |
| 17 | 1.139 s | 1.356 s |
| 18 | 1.490 s | 1.521 s |
| 19 | 1.268 s | 1.574 s |
| 20 | 6.035 dd | 6.085 dd |
| 21E | 5.178 br d | 5.355 br d |
| 21Z | 5.163 br d | 5.326 br d |

We claim:

1. A compound selected from hapalindole J and hapilandole M of the formula:

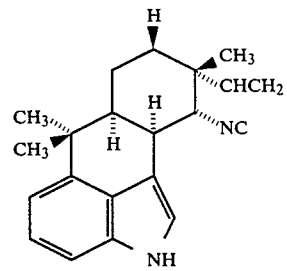

wherein R¹ is —NC (hapalindole J) or —NCS (hapalindole M).

2. The compound of claim 1 wherein R¹ is —NC.

3. The compound of claim 1 wherein R¹ is —NCS.

4. Hapalindole K of the formula:

5. Hapalindole L of the formula:
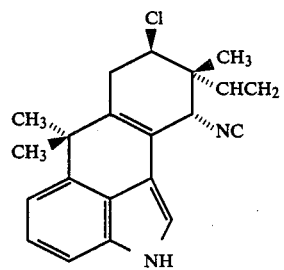
6. Hapalindole O of the formula:
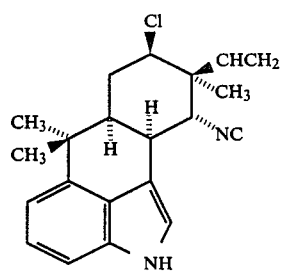
7. A compound of the formula
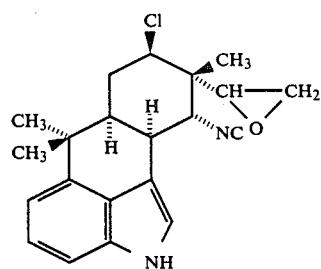
8. The compound of claim 7 wherein the hydrogen at C-20 is in the "R" chirality.
9. The compound of claim 7 wherein the hydrogen at C-20 is in the "S" chirality.
10. Hapalindole Q of the formula:
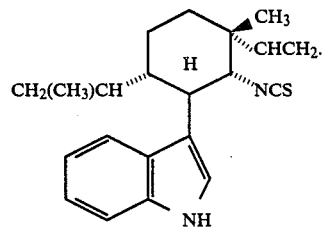
11. Hapalindole T of the formula
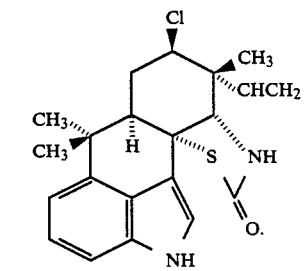
12. Hapalindole U of the formula
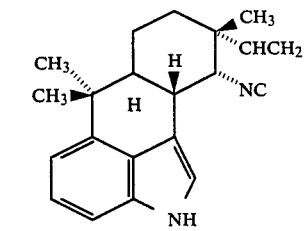
13. Hapalindole V of the formula
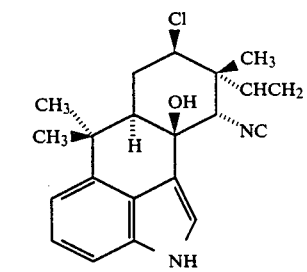
* * * * *

UNITED STATES PATENT AND TRADEMARK OFFICE
CERTIFICATE OF CORRECTION

PATENT NO. : 4,870,185
DATED : September 26, 1989
INVENTOR(S) : R. Bonjouklian, et al.

It is certified that error appears in the above-identified patent and that said Letters Patent is hereby corrected as shown below:

In column 12 at lines 50-57:

" 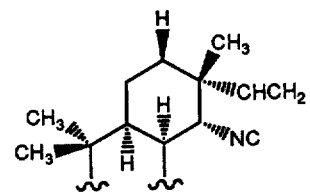 " 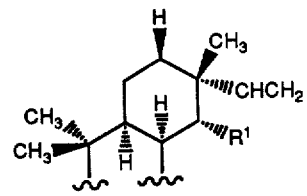

Should read --                                    --.

In column 14 at lines 6-12:

" 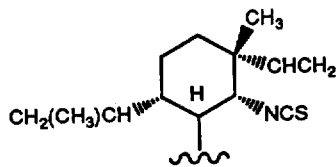 " 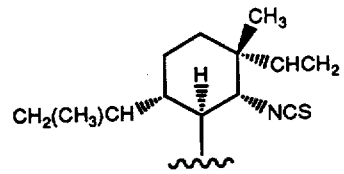

Should read --                                    --.

UNITED STATES PATENT AND TRADEMARK OFFICE
CERTIFICATE OF CORRECTION

PATENT NO. : 4,870,185

DATED : September 26, 1989

INVENTOR(S) : R. Bonjouklian, et al.

It is certified that error appears in the above-identified patent and that said Letters Patent is hereby corrected as shown below:

In column 14 at lines 32-38:

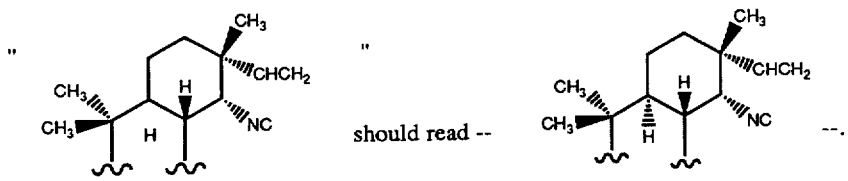

Signed and Sealed this

Twentieth Day of November, 1990

Attest:

HARRY F. MANBECK, JR.

Attesting Officer

Commissioner of Patents and Trademarks